United States Patent [19]

Fryberg et al.

[11] 4,359,521
[45] Nov. 16, 1982

[54] LIGHT-SENSITIVE COLOR PHOTOGRAPHIC MATERIAL

[75] Inventors: Mario Fryberg, Praroman-le-Mouret; Remon Hagen, Marly, both of Switzerland; John G. V. Scott, Little Baddow, England

[73] Assignee: Ciba-Geigy AG, Basel, Switzerland

[21] Appl. No.: 105,174

[22] Filed: Dec. 19, 1979

Related U.S. Application Data

[63] Continuation of Ser. No. 945,153, Sep. 22, 1978, abandoned.

[30] Foreign Application Priority Data

Sep. 29, 1977 [CH] Switzerland ............... 11906/77
Dec. 29, 1977 [CH] Switzerland ............... 16180/77

[51] Int. Cl.³ .................................................. G03C 1/40
[52] U.S. Cl. ...................................... 430/505; 430/382; 430/544; 430/557; 430/558; 430/957
[58] Field of Search ............... 430/505, 544, 557, 558, 430/957, 382

[56] References Cited

U.S. PATENT DOCUMENTS

| | | | |
|---|---|---|---|
| 3,933,500 | 1/1976 | Shiba et al. | 430/554 |
| 4,015,988 | 4/1977 | Shiba et al. | 430/505 |
| 4,046,575 | 9/1977 | Boie et al. | 430/557 |
| 4,182,630 | 1/1980 | Quaglia | 430/558 |
| 4,248,961 | 2/1981 | Hagen et al. | 430/558 |

FOREIGN PATENT DOCUMENTS 7605615 11/1976 Netherlands .

*Primary Examiner*—J. Travis Brown
*Attorney, Agent, or Firm*—Joseph G. Kolodny

[57] ABSTRACT

Light-sensitive color photographic material which contains on a base in at least one silver halide emulsion layer or an interlayer which is assigned to this and does not contain silver halide, at least one DIR coupler of the formula

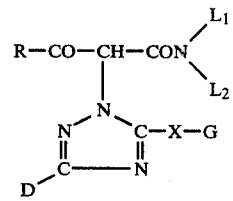

in which R is alkyl having 1 to 18 carbons atoms or aryl, D is hydrogen, optionally substituted alkyl having 1 to 18 carbon atoms, cycloalkyl having 3 to 10 carbon atoms, alkenyl having 2 to 18 carbon atoms, cycloalkenyl having 5 to 10 carbon atoms, aralkyl having 7 to 18 carbon atoms, cyano or halogen and G is a optionally substituted aliphatic hydrocarbon radical having 1 to 18 carbon atoms, the sum of the carbon atoms in the substituents D and G being at least 5, $L_1$ is hydrogen or alkyl having 1 to 5 carbon atoms, $L_2$ is alkyl having 1 to 18 carbon atoms, phenyl or phenyl substituted by halogen, alkyl or alkoxy, each having 1 to 18 carbon atoms, acylamino, sulphonamide groups or carboxamide groups and X is sulphur or selenium, and wherein the triazolyl radical released during the reaction of the coupler with an oxidation product of an aromatic developer containing primary amino groups has development-inhibiting effects.

The DIR-couplers can contribute substantially to improving interlayer color correction and to the image grain and the sharpness of the photographic images obtained after imagewise exposure and usual processing of said photographic material.

7 Claims, No Drawings

LIGHT-SENSITIVE COLOR PHOTOGRAPHIC MATERIAL

This is a continuation of Application Ser. No. 945,153, filed Sept. 22, 1978, now abandoned.

The present invention relates to photographic couplers, especially yellow couplers, which release development inhibitors, light sensitive colour photographic materials which contain these couplers and a method of forming a visible image by imagewise exposing and colour-development processing of said photographer material.

It is known to treat the exposed silver halide in a light-sensitive silver halide emulsion layer in the presence of colour couplers with a developer containing primary aromatic amines, in order to produce coloured photographic images.

Colour couplers for forming the yellow dye as a rule contain active methylene groups which during colour developing react with the oxidised colour developer, four equivalents of developable silver halide being required. If one hydrogen atom of the methylene group has been replaced by a group detachable during the coupling reaction, only two equivalents of developable silver halide are required to form the dye. A large number of leaving groups for the so-called 2-equivalent yellow couplers are already known and include, inter alia, triazolyl and tetrazolyl leaving groups (cf. German Offenlegungsschrift No. 2,442,703 and German Offenlegungsschrift No. 2,528,638).

It is also known to add to materials for colour photography compounds which, during the reaction with the colour developer oxidation products, release development inhibitors. Such compounds are the so-called DIR couplers (DIR=development inhibitor releasing). The inhibitors released during developing from the DIR couplers as a function of the image density can produce a so-called intralayer effect in the emulsion layer, i.e. they improve the colour tint, the fineness of the image grain and the sharpness of the image, since they are able to inhibit development in accordance with the image density. If they diffuse into other layers, they have a so-called masking development inhibiting effect in the other layers, this effect depending on the image density in the original emulsion layer. In the case of exposure to polychromatic light, they have a so-called interlayer effect, in that they lead to an improvement in the colour in other layers, as a result of the development inhibition. Usually, both intralayer and interlayer effects are to be expected.

For the mechanism of this effect see, for example, Barr, Thirtle and Vittum, Photographic Science Engineering 13, 214 (1969). Known DIR couplers release, for example, halide ions, especially the iodide ion, benztriazolyl radicals (benztriazole compounds) or mercapto and selenyl radicals (compounds) of the formulae

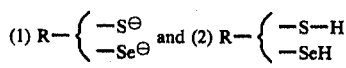

in which R is alkyl or aryl or a heterocyclic radical, as diffusible radicals (compounds), during the coupling reaction. (U.S. Pat. Nos. 3,227,554 and 3,632,345; German Offenlegungsschriften Nos. 2,255,032, 2,427,183, 2,502,892, 2,509,341, 2,523,705, 2,540,959 and 2,636,347).

These radicals (compounds) can then influence development, either in the same layer or in an adjacent layer.

Because the radicals which are released from the DIR couplers and inhibit development have differing adsorptions (R. J. Newmiller and R. B. Pontius, Phot. Sci. Eng. 5, 283 (1961)) on the active silver halide centres, their development inhibiting effect is either too great (for example in the case of the thioether radicals RSH or RS$^\ominus$) or relatively weak (for example in the case of I$^\ominus$ and the released benztriazolyl radicals).

The known DIR couplers are therefore not able to meet the demands made on them in all respects since, in particular, they also have one or more of the following disadvantages:

delay in development of the layer containing the DIR couplers, a not very pronounced interlayer colour correction, levelling off of the gradation, a reduction in the sensitivity and a reduction in the maximum colour density, i.e. the colour formed from the colour-producing couplers.

The object of the present invention is, therefore, to provide novel compounds which release development inhibitors during the reaction with colour developer oxidation products and do not possess the abovementioned disadvantages or at least are able substantially to eliminate these.

It has now been found that the compounds of the formula (5) given below are outstandingly suitable as DIR couplers and can contribute substantially to improving the image grain and the sharpness of the image, to transforming the gradation curve to a straight line and to interlayer colour correction. The DIR coupler characteristics of the compounds of the formula (5) are also surprising inasmuch as it is known from German Offenlegungsschrift No. 2,547,691 (page 4) that 5-mercaptotetrazoles of the formula

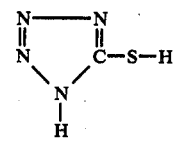

or 3-mercaptotriazoles of the formula

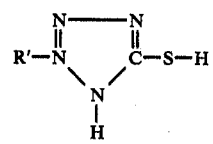

do not have any development-inhibiting effects.

The present invention relates to a light-sensitive colour photographic material which contains, on a base, in at least one silver halide emulsion layer or an interlayer which is assigned to this and does not contain silver halide, at least one DIR coupler of the formula

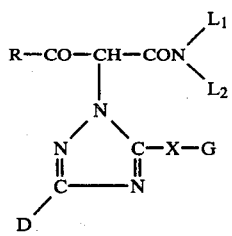

in which R is straight-chain or branched alkyl having 1 to 18 carbon atoms or aryl, D is hydrogen, substituted or unsubstituted alkyl having 1 to 18 carbon atoms, cycloalkyl having 3 to 10 carbon atoms, alkenyl having 2 to 18 carbon atoms, cycloalkenyl having 5 to 10 carbon atoms, aralkyl having 7 to 18 carbon atoms, cyano or halogen and G is a substituted or unsubstituted aliphatic hydrocarbon radical having 1 to 18 carbon atoms, the sum of the carbon atoms in the substituents D and G being at least 5, $L_1$ is hydrogen or alkyl having 1 to 5 carbon atoms, $L_2$ is alkyl having 1 to 18 carbon atoms, phenyl or phenyl substituted by halogen, alkyl or alkoxy, each having 1 to 18 carbon atoms, acylamino, sulphonamide groups or carboxamide groups and X is sulphur or selenium, and wherein the triazolyl radical released during the reaction of the coupler with an oxidation product of an aromatic developer containing primary amino groups has development-inhibiting effects.

The present invention also relates to the novel DIR couplers of the formula (5) and to a method of forming a visible image, which comprises treating the colour photographic material according to the invention after imagewise exposure, with a developer solution containing an aromatic primary amine.

The invention also relates to the coloured photographic images obtained by this method.

The radical R in the compounds of the formula (5) is alkyl having 1 to 18 carbon atoms and these alkyl radicals can be straight-chain or branched, for example methyl, ethyl, n-propyl, iso-propyl, n-butyl, iso-butyl, tert.-butyl, amyl, iso-amyl, tert.-amyl, 1,1,3,3-tetramethylbutyl, 1-methyl-1-ethylpentyl, hexyl, 1-methylpentyl, neopentyl, 1-, 2- or 3-methylhexyl, heptyl, n-octyl, tert.-octyl, 2-ethylhexyl, n-nonyl, isononyl, tert.-nonyl, decyl, tert.-decyl and undecyl; and also dodecyl, tetradecyl, hexadecyl and octadecyl and their isomers. Particularly suitable radicals are straight-chain or branched alkyl radicals having 3 to 10 carbon atoms, and amongst these tert.-alkyl radicals having 4 to 8 carbon atoms are preferred. Tert.-butyl, 1,1,3,3-tetramethylbutyl, 1-methyl-1-ethylpentyl and 1,1-dimethylpentyl are particularly preferred tertiary alkyl radicals.

These alkyl radicals can be substituted by halogen atoms, especially fluorine, chlorine (for example —$CH_2Cl$, —$CCl_3$) or bromine; hydroxyl, nitro, cyano or alkoxy, especially having 1 to 5 carbon atoms in the alkoxy moiety, for example —$CH_2$—O—$C_nH_{2n+1}$, in which n is 1 to 5.

If R is aryl, this is in particular phenyl or substituted phenyl and the substituents can be alkyl or alkoxy, each having 1 to 4 carbon atoms, for example methyl, ethyl, propyl, butyl and isomeric radicals; further substituents are halogen, especially chlorine and bromine, or the divalent radicals —$OCH_2O$— and —$OCH_2CH_2O$—, which are bonded to adjacent carbon atoms of the phenyl ring and together with this form a 5-membered or 6-membered ring.

The radical D in the compounds of the formula (5) is hydrogen, alkyl having 1 to 18 carbon atoms (as indicated above for R), which can be substituted by halogen, such as chlorine or bromine, nitro, cyano, amino or alkoxy having 1 to 18 carbon atoms; cycloalkyl which has 3 to 10 and especially 6 to 10 carbon atoms and can have 1 to 4 cycloalkyl rings, for example cyclopropyl, cyclobutyl, cyclopentyl, cyclohexyl, norbornyl or 1-adamantyl, the four last-mentioned radicals being preferred; or alkenyl having 2 to 18 carbon atoms, possible radicals being the unsaturated radicals which correspond to the radicals named under alkyl. If D is cycloalkenyl, such radicals are those having 5 to 10 and especially 5 and 6 carbon atoms, for example cyclohexenyl, whilst radicals suitable as aralkyl having 7 to 18 carbon atoms are, in particular, the phenyl-substituted alkyl radicals, such as benzyl and phenylethyl, and also the homologous alkyl radicals up to dodecyl. D is also cyano or halogen, especially chlorine or bromine.

The substituent G is a substituted or unsubstituted aliphatic hydrocarbon radical having 1 to 18 carbon atoms, especially an alkyl radical having the said number of carbon atoms, and such radicals can be straight-chain or branched (see the corresponding data for R). These alkyl radicals can be substituted by halogen atoms, especially by fluorine, chlorine or bromine, and also by hydroxyl, nitro, cyano or alkoxy, especially having 1 to 5 carbon atoms in the alkoxy moiety, for example —$CH_2OC_nH_{2n-1}$, in which n is 1 to 5. Further substituents on the alkyl can be aryl, especially phenyl or substituted phenyl; the benzyl radical is the preferred representative of aryl-substituted alkyl.

The sum of the number of carbon atoms in the substituents D and G must be at least 5.

The substituent $L_1$ is, in addition to hydrogen, alkyl having 1 to 5 carbon atoms, for example methyl, ethyl, propyl, iso-propyl, butyl, iso-butyl, tert.-butyl or amyl, iso-amyl and tert.-amyl. The substituent $L_2$ is alkyl having 1 to 18 carbon atoms and possible radicals are the straight-chain or branched alkyl radicals named under R. Furthermore, $L_2$ is phenyl or substituted phenyl containing the substituents halogen, especially fluorine, chlorine and bromine, alkyl or alkoxy, each having 1 to 18 carbon atoms (cf. the radicals indicated for R), acylamino (especially derived from carboxylic acids), sulphonamide (including those with substituents on the nitrogen atom) or carboxamide (including those with substituents on the nitrogen atom). The substituents on the acylamino or carbox(sulphon)amido groups are, as a rule, ballast groups which are customary for colour couplers and are known per se. The substituted phenyl radical can contain one or more of the indicated substituents.

A substituted phenyl of the formula

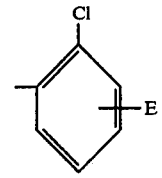

is preferred, in which E is, in particular, in the 5-position and is straight-chain or branched alkyl having 10 to 18 carbon atoms, alkyl-substituted phenoxy (one or more alkyl substituents having 1 to 8 carbon atoms) or alkoxy-substituted phenyl (one or more alkoxy substituents, which can be further substituted), and E can be bonded directly or indirectly, for example via an alkylene bridge member via —CONH—, —NHCO—, —SO₂NH—, —NHSO₂— or other bridge members to the phenyl ring.

Preferred colour photographic materials are those which contain a DIR coupler of the formula

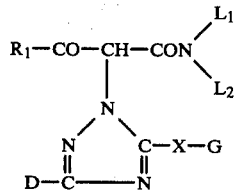
(7)

in which R₁ is straight-chain or branched alkyl having 3 to 10 carbon atoms, phenyl or phenyl substituted by halogen, alkyl or alkoxy, each having 1 to 4 carbon atoms, or the radicals —OCH₂O— and —OCH₂CH₂O—, and D, G, L₁, L₂ and X are as defined, or contain a DIR coupler of the formula

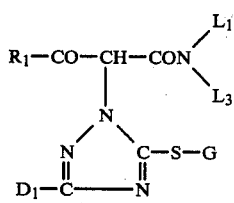
(8)

in which D₁ is hydrogen, alkyl having 1 to 4 carbon atoms, benzyl or chlorine and L₃ is phenyl or phenyl substituted by alkoxy having 1 to 5 carbon atoms, chlorine, acylamino or carboxamide, the two last mentioned radicals optionally carry ballast groups on the nitrogen atoms, and R₁, L₁ and G are as defined.

Particularly suitable colour photographic materials are furthermore those which contain DIR couplers of the following formulae (9) and (10) and particularly preferentially of the formulae (11) to (13):

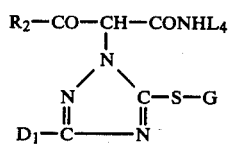
(9)

in which R₂ is phenyl, tert.-butyl or a radical of the formulae

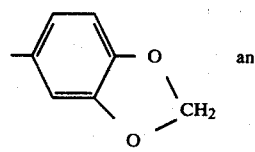 and 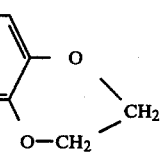

and L₄ is a radical of the formula

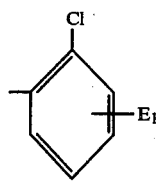

in which E₁ is a radical of the formulae

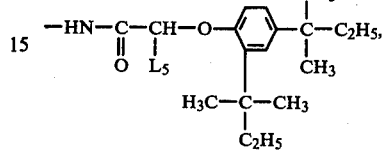

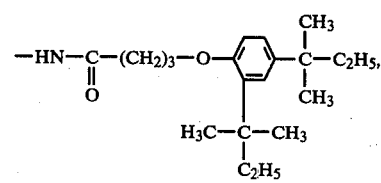

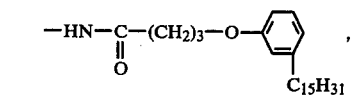

,

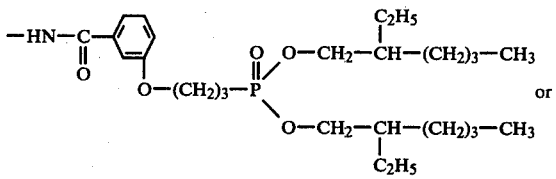

or

-continued

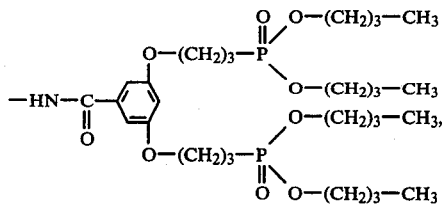

in which $L_5$ is hydrogen, ethyl or n-dodecyl, $L_6$ is n-dodecyl or n-octadecyl and n is a number from 8 to 18, and $D_1$ and G are as defined;

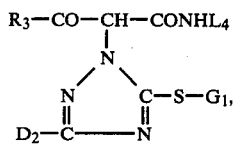
(10)

in which $R_3$ is phenyl or tert.-butyl, $G_1$ is alkyl having 1 to 18 carbon atoms or benzyl and $D_2$ is hydrogen, methyl, ethyl, propyl or butyl, the sum of the carbon atoms in the substituents $D_2$ and $G_1$ being at least 5, and $L_4$ is as defined;

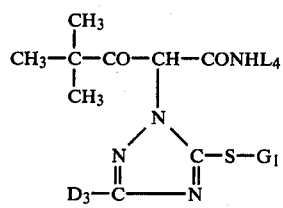
(11)

in which $D_3$ is hydrogen or methyl, the sum of the carbon atoms in the substituents $D_3$ and $G_1$ is at least 5 and $G_1$ and $L_4$ are as defined;

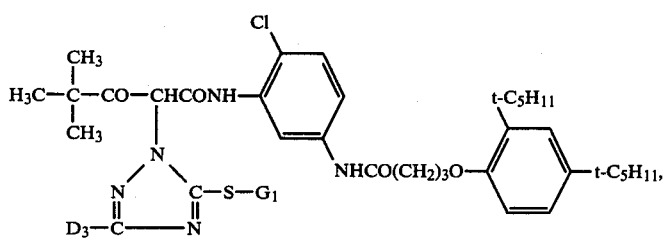
(12)

in which $D_3$ and $G_1$ are as defined; and

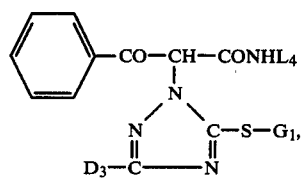
(13)

in which $D_3$ is hydrogen or methyl and $G_1$ is alkyl having 1 to 18 carbon atoms or benzyl, the sum of the carbon atoms in the substituents $D_3$ and $G_1$ is at least 5 and $L_4$ is as defined.

If X in the general formula (5) is selenium, the DIR couplers indicated in the following formulae (14) to (19) result and these are also suitable for incorporation in photographic materials. Photographic materials which contain the DIR couplers of the formulae (17) to (19) are particularly preferred:

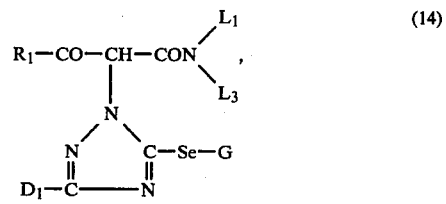
(14)

in which $D_1$ is hydrogen, alkyl having 1 to 4 carbon atoms, benzyl or chlorine and $L_3$ is phenyl or phenyl substituted by alkoxy having 1 to 5 carbon atoms, chlorine, acylamino or carboxamide, the two last-mentioned radicals optionally carry ballast groups on the nitrogen atoms, and $R_1$, $L_1$ and G are as defined;

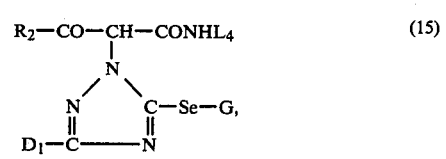
(15)

in which $R_2$, $D_1$, G and $L_4$ are as defined;

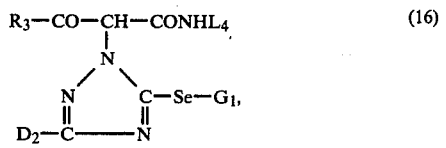
(16)

in which $R_3$, $D_2$, $G_1$ and $L_4$ are as defined;

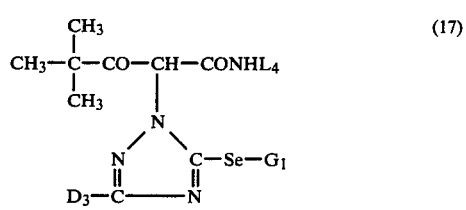
(17)

in which $D_3$, $G_1$ and $L_4$ are as defined;

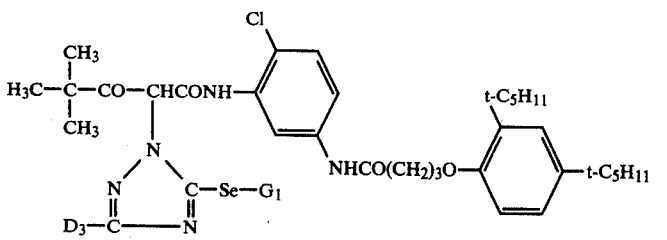
(18)

in which $D_3$ is as defined and $G_1$ is alkyl having 1 to 18 carbon atoms and especially 4 to 12 carbon atoms, or benzyl; and

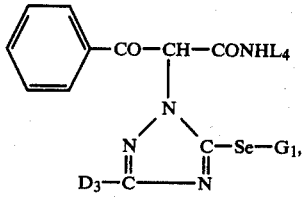
(19)

in which $D_3$, $G_1$ and $L_4$ are as defined.

The DIR couplers of the formula (5) can be obtained, for example, by reacting halogen compounds of the formula

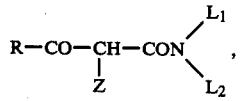
(20)

in which Z is a halogen atom, preferably chlorine or bromine, and R, $L_1$ and $L_2$ are as defined, with triazoles of the formula

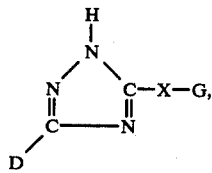
(21)

in which D, G and X are as defined. The reaction is advantageously carried out in an inert organic solvent, for example acetonitrile, propionitrile or dimethylformamide, and in the presence of an acid-binding agent.

In place of the triazoles, it is possible to use salts of these compounds, especially alkali metal salts, as starting materials, with an equally good result.

The azeniate ion which corresponds to the triazole can also be produced independently and then reacted with the compounds of the formula (20). This azeniate ion, which first is also formed from the triazole and the acid-binding agent, has a formula to which the following corresponding mesomeric structures can be assigned:

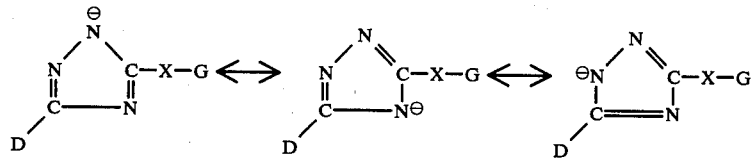

In accordance with the relative electron density on the individual nitrogen atoms of the ring, which, in turn, is dependent on the substituents X-G and D, the reaction with the compounds of the formula (20) can now take place at one of these N atoms. By this means, the various isomeric compounds then form. This behaviour has been described in the literature in the case of related reactions of triazoles (in this context cf. J. Het. Chem. 12, 855 (1975); Bull. Soc. Chim. France 1973, 323; 1975, 647). (A precise assignment of a structure to the individual isomers is exceptionally time-consuming, even in simple cases; cf. the cited literature). It has been found that, in the cases examined here, this isomerism, if it occurs at all, has no influence on the desired properties in use. For this reason, a detailed description of all of the isomeric forms possible in each case is not given. It is, however, self-evident that each of the possible isomeric forms can be used for the desired application.

The α-halogeno-acylacetanilides which are known to those skilled in the art and are described, inter alia, in German Offenlegungsschrift No. 2,114,577, French Pat. Nos. 991,453 and 869,169 and U.S. Pat. Nos. 2,728,658 and 3,277,155, can be employed as compounds of the formula (20), which are used for the synthesis of the photographic couplers according to the invention.

Thus, for example, the following compounds can be used:

1. α-Acetyl-α,2-dichloro-5-[α-(2',4'-di-tert.-amylphenoxy)-acetylamino]-acetanilide
2. α-Pivaloyl-α-bromo-2-chloro-5-[α'-(4'-tert.-amylphenoxy)-n-tetradecanoylamino]-acetanilide
3. α-(β'-Methoxy-α',α'-dimethyl-propionyl)-α-chloro-4-[N-(γ''-phenylpropyl)-N-(p-tolyl)carbamoylmethoxy]acetanilide
4. α-(α'-Methoxyisobutyryl)-α-chloro-2-methoxy-5-[γ-(3''-n-pentadecylphenoxy)-butyramino]-acetanilide
5. α-(α'-Phenoxyisobutyryl)-α,2-dichloro-5-(n-octadecylsuccinimido)-acetanilide
6. 1-[α-(α',α'-Dimethylbutyryl)-α-chloroacetylamino]-2-phenoxybenzene-5-carboxylic acid (di-n-butoxy)-phosphono-ethylamide [—CO—NH—CH$_2$—CH$_2$—(OP)(O—C$_4$H$_9$)$_2$]
7. α-(α',α'-Dimethyl-octadecanoyl)-α-bromo-3,5-bis-methoxycarbonyl-acetanilide 8. α-(α'-Ethyl-α'-methyl-hexanoyl)-α-bromo-2-chloro-5-[γ"-(2",4"-di-tert.-amylphenoxy)-butyramino]-acetanilide 9. α-(α',α',γ',γ'-Tetramethyl-valeryl)-α,2-dichloro-5-(n-dodecyloxycarbonyl)-acetanilide 10. α-(1'-Methyl-cyclohexanecarbonyl)-α-bromo-2-chloro-5-[α"-(2",4"-di-tert.-amylphenoxy)-butyramino]-acetanilide 11. α-(7',7'-Dimethylnorbornane-1'-carbonyl)-α,2-dichloro-5-[α"-(2",4"-di-tert.-amylphenoxy)-acetamino]-acetanilide 12. α-Benzoyl-α-chloro-2-methoxy-5-[α'-(3'-n-dodecyloxyphenoxy)-butyramino]-acetanilide 13. 1-[α-(4'-Methoxybenzoyl)-α-chloro]-acetylamino-2-chloro-5[β-(N-palmityl-N-n-butyl-amino)-propionylamino]-benzene 14. α-Piperonyloyl-α,2-dichloro-5-(α'-phenoxy-n-tetradecanoylamino)-acetanilide 15. (α'-n-dodecyloxycarbonyl)-ethyl 1-[α-(2'-chlorobenzoyl)-α-chloro]-acetylaminobenzene-4-carboxylate 16. α-(4'-Chlorobenzoyl)-α-bromo-2-hexadecyloxy-acetanilide 17. α-Piperonyloyl-α-chloro-3-[(N-methyl-N-n-octadecyl)-sulphamoyl]-acetanilide 18. α-{3'-[γ-(2',4"-Di-t-amylphenoxy)-butyramino]-benzoyl}-α-bromo-4-chloro-2,5-dimethoxy-acetanilide 19. α-{3'-[α"-(3"-n-pentadecylphenoxy)-butyramino]-benzoyl}-α,2-dichloro-acetanilide 20. α-(4'-n-Hexadecyloxy-benzoyl)-α-chloro-2-methoxyacetanilide 21. α-Pivaloyl-2-chloro-5-[γ-(2,4-di-t-amylphenoxy)-butylamido]-acetanilide.

The triazoles of the formula (21) are also prepared by known processes. The mercapto- and seleno-triazoles can be obtained, for example, by reacting thio(seleno)-semicarbazides with corresponding acid amides; further reaction with alkyl halides or alkylaryl halides then gives the compounds of the formula (21).

The DIR couplers, according to the invention, of the formula (5) can be incorporated in at least one of the layers of a light-sensitive chromogenic multi-layer colour photographic material, for example in the silver halide emulsion layers of a light-sensitive multi-layer colour photographic material and the layers which adjoin or are assigned to the silver halide emulsion layers, for example a yellow filter layer, an antihalation layer, an interlayer and/or a protective layer. In the present context, an assigned layer is to be understood as meaning a layer which is spatially so arranged relative to the light-sensitive silver halide emulsion layer that, during developing of the silver halide emulsion layer, colour developer oxidation products can diffuse from this layer into the assigned layer in an amount which produces the desired effect.

The DIR couplers can also be present in developer solutions for the light-sensitive multi-layer colour photographic material or can also at the same time be present in the developer solutions and in the photographic material.

The light-sensitive colour photographic material according to the invention, which contains on a base in at least one silver halide emulsion layer or an interlayer which is assigned to the latter and does not contain silver halide a DIR-coupler of the formula (5), can be, for example, a photographic multi-layer material which contains on a base first a red-sensitive photographic silver halide emulsion layer, then a green-sensitive photographic silver halide emulsion layer and then a blue-sensitive photographic silver halide emulsion layer, together with customary interlayers and further auxiliary layers.

These light-sensitive silver halide emulsion layers usually contain at least one non-diffusing colour coupler to produce an image dye of a colour which as a rule is complementary to the spectral sensitivity. Thus, the red-sensitive layer contains, for example, a non-diffusing phenol or α-naphthol colour coupler to produce the cyan partial colour image, the green-sensitive layer contains at least one non-diffusing 5-pyrazolone, pyrazolonebenzimidazole or indazolone colour coupler to produce the magenta partial colour image and the blue-sensitive layer finally contains at least one non-diffusing colour coupler to produce the yellow partial colour image, a colour coupler containing an open-chain ketomethylene grouping usually being employed for this purpose. A large number of colour couplers of these types are known and these have been described in a large number of publications.

The DIR couplers of the formula (5) can be incorporated in one of the said red-sensitive, green-sensitive or blue-sensitive silver halide layers or in layers which are assigned (adjacent) to the latter and are free from silver halide and as a rule hydrophilic. Preferred layers for incorporation of the DIR (yellow) couplers are the blue-sensitive silver halide layer or the layer or layers assigned to this layer. The inhibiting effect of the DIR couplers according to the invention can arise both in the silver halide emulsion layer which contains the DIR coupler and in adjacent silver halide emulsion layers, into which the released inhibitor diffuses. In this way, it is possible to control developing in each individual light-sensitive silver halide emulsion layer by, for example, influencing, by means of adjacency effects, developing in one silver halide layer by another layer which is developed image-wise and thus, for example, to achieve an improvement in the fineness of the image grain, in the sharpness of the image and in the colour shade.

When the DIR couplers according to the invention are used in conventional silver halide emulsions and in combination with non-diffusing colour couplers, negative images are usually obtained. However, the DIR couplers are also suitable for producing positive images by known reversal processes, the photographic material first being subjected, after image-wise exposure, to black-and-white developing in order to produce a silver negative image and the silver halide in the areas not previously developed then being fogged and subjected to colour-developing and positive coloured images thus being obtained.

The DIR couplers according to the invention and also the colour couplers are added by known methods to the light-sensitive silver halide emulsions or to the coating solutions for the production of the other layers. Solvents which can be used for incorporation are solvents which do not have an adverse effect on the properties of the silver halide emulsions, for example water, methanol, ethanol, acetone, ethyl acetate, dimethylformamide, dibenzyl phthalate, tricresyl phosphate or mixtures of the said organic solvents, especially with water. The amount of the DIR couplers used according to the invention varies depending on the nature of the light-sensitive multi-layer material, for colour photography, which is to be used and also depending on the type of developing; as a rule it is, however, in a range from 0.5 to 100 g per mol of silver halide if the DIR coupler is incorporated in the silver halide emulsion layer of a light-sensitive multi-layer colour photographic material, in a range from 0.020 to 15 g per 100 g of gelatin if the DIR coupler is incorporated in a layer which is adjacent to the silver halide emulsion layer or in another auxiliary layer and, furthermore, in a range from 0.0001 g to 1 g, preferably from 0.005 to 0.5 g, per liter of developer solution, if the DIR coupler is added to the developer solution.

As a rule, the DIR couplers can be present in an amount of 0.1 to 100 percent by weight [weight ratio (0.001–1):1], preferably in an amount of 0.1 to 60 or 50 percent by weight, especially 0.2 to 50 percent by weight, based on the colour-producing coupler or couplers, in the silver halide layer or in an interlayer or auxiliary layer which is assigned to the silver halide layer and does not contain silver halide, and the total amount of the DIR couplers, based on the amount of all couplers (colour couplers and DIR couplers) in the photographic material, should preferably be at most about 20 percent by weight.

If the DIR couplers according to the invention are used in photographic developer solutions, the developer solution generally contains an aromatic primary amine as the developer substance, preferably a p-phenylenediamine derivative, for example 4-amino-N,N-dimethylaniline, 4-amino-N,N-diethylaniline, 4-amino-3-methyl-N-methyl(ethyl)-N-($\beta$-methyl-sulphonamidoethyl)-aniline, 4-amino-3-methyl-N-ethyl-N-($\beta$-hydroxyethyl)-aniline, monomethyl-p-phenylenediamine, N-butyl-N-$\omega$-sulphobutyl-p-phenylenediamine or N,N-bis-($\beta$-hydroxyethyl)-p-phenylenediamine.

In order to increase the interlayer effect, the light-sensitive multi-layer material for colour photography can be developed at conventional developing temperatures, i.e. at 20° to 30° C.; if desired, however, developing can also be carried out at temperatures of, for example, 30° to 80° C. or even at still higher temperatures.

The silver halide emulsions used to prepare the photographic material according to the invention can contain, for example, silver bromide, silver iodide, silver chloride, silver chloride/bromide, silver iodide/bromide and silver chloride/iodide/bromide. Good results are also obtained when at least one photographic emulsion layer which contains silver chloride/iodide, silver iodide/bromide or silver chloride/iodide/bromide with an iodine content of 1 to 20 mol % is used.

The emulsions can be conventional negative or direct positive emulsions. The emulsions can contain the customary additives, for example hardeners, sensitisers, stabilisers, wetting agents and antifogging agents.

The binder used for the photographic layers is preferably gelatin. This can, however, be entirely or partially replaced by other naturally occurring or synthetic binders. Suitable naturally occurring binders are, for example, alginic acid and its derivatives, such as salts, esters or amides, cellulose derivatives such as carboxymethylcellulose or an alkylcellulose such as hydroxyethylcellulose, or starch and its derivatives, such as ethers or esters. Synthetic binders are, for example, acrylic resins, polyvinyl alcohol, partially saponified polyvinyl acetate or polyvinylpyrrolidone.

Layer supports for the photographic material according to the invention are the films which are customary and suitable for this purpose, for example made of cellulose nitrate, cellulose acetate, such as cellulose triacetate, polystyrene, polyesters, such as polyethylene terephthalate, or polyolefins, such as polyethylene or polypropylene, and also papers, which can be coated, for example polyethylene-coated papers, as well as glass.

In the following preparation instructions and examples, parts and percentages are by weight unless otherwise stated.

PREPARATION INSTRUCTIONS

Preparation Instruction 1

3(5)-Mercapto-1,2,4-triazole

A mixture of 182 g (2 mols) of thiosemicarbazide and 140 g of formamide is stirred at 180° C. until no further ammonia is evolved. The excess formamide is removed in vacuo. The residue is recrystallised from water. 148 g of a colourless compound are obtained. Melting point: 222° to 225° C.

Preparation Instruction 2

3(5)-Heptylmercapto-1,2,4-triazole 50.5 g (0.5 mol) of 3(5)-mercapto-triazole are added to a solution of 28 g (0.5 mol) of potassium hydroxide in 500 ml of absolute methanol. The mixture is stirred at about 30° C. for 30 minutes.

90 g of n-heptyl bromide are added and the solution is refluxed for 12 hours. The salt which has precipitated is filtered off and the solution is then evaporated. The resulting crude product is recrystallised from toluene. 83 g of 3(5)-heptylmercapto-1,2,4-triazole are obtained. Melting point: 69° to 73° C.

The other triazoles in Table 1 were prepared analogously.

TABLE 1

Compounds of the general formula (100)

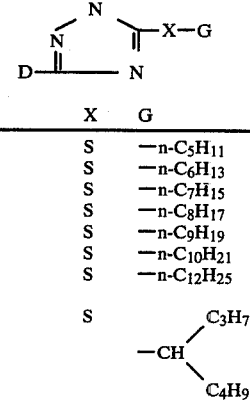

| No. | D | X | G | Melting point °C. |
|---|---|---|---|---|
| 101 | H | S | —n-$C_5H_{11}$ | 74–76 |
| 102 | H | S | —n-$C_6H_{13}$ | 71–73 |
| 103 | H | S | —n-$C_7H_{15}$ | 69–73 |
| 104 | H | S | —n-$C_8H_{17}$ | 71–72 |
| 105 | H | S | —n-$C_9H_{19}$ | 68–70 |
| 106 | H | S | —n-$C_{10}H_{21}$ | 152–155 |
| 107 | H | S | —n-$C_{12}H_{25}$ | 76–79 |
| 108 | H | S | 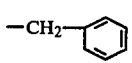 | 56–59 |
| 109 | H | S | —n-$C_{18}H_{37}$ | 98–101 |
| 110 | H | S | 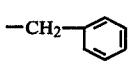 | 74–75 |
| 111 | $CH_3$ | S | 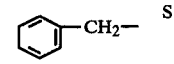 | 123–126 |
| 112 | ⌬—$CH_2$— | S | —$CH_3$ | 150–154 |
| 113 | —n-$C_3H_7$ | S | —n-$C_4H_9$ | 72–74 |
| 114 | —$CH_3$ | Se | —n-$C_8H_{17}$ | 67–70 |
| 115 | H | S | —n-$C_4H_9$ | 33–35 |
| 116 | $CH_3$— | Se | —n-$C_6H_{13}$ | 70–72 |
| 117 | $CH_3$— | Se | —n-$C_7H_{15}$ | 67–69 |

TABLE 1-continued

Compounds of the general formula (100)

$$\underset{D}{\overset{N}{\underset{\|}{\diagdown}}}\underset{N}{\overset{\overset{H}{\underset{|}{N}}}{\diagup}}-X-G$$

| No. | D | X | G | Melting point °C. |
|-----|-----|-----|-----------|-------|
| 118 | $CH_3-$ | Se | $-n-C_4H_9$ | 96–97 |
| 119 | $CH_3-$ | Se | $-n-C_{10}H_{21}$ | 64–66 |
| 120 | $CH_3-$ | Se | $-n-C_{12}H_{25}$ | 73–74 |

Preparation Instruction 3

α-[3(5)-Heptylmercapto-1,2,4-triazolyl]-α-pivaloyl-2-chloro-5-[γ-(2,4-di-t-amylphenoxy)-butylamido]-acetanilide A mixture of 9.75 g (0.015 mol) of α-pivaloyl-α-bromo-2-chloro-5-[γ-(2,4-di-t-amylphenoxy)-butylamido]acetanilide, 4 g (0.02 mol) of 3(5)-heptylmercapto-1,2,4-triazole and 1.12 g (0.02 mol) of potassium hydroxide is stirred in 150 ml of acetonitrile for 10 hours at room temperature. After cooling in ice, the salt which has precipitated is filtered off and the acetonitrile is removed from the filtrate in vacuo. The residue is taken up in methanol and added slowly dropwise to an excess of water, the pH value of which has been adjusted to 2 to 3 with hydrochloric acid. The precipitate is filtered off. After drying, the product is recrystallised from ether/hexane.

4.8 g of the compound of the formula

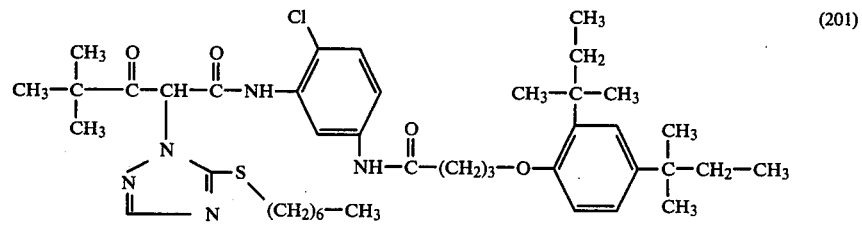
(201)

are obtained. Melting point: 140° to 142° C.

The compounds in Table 2 are obtained analogously from the corresponding starting materials (cf. the triazoles in Table 1):

TABLE 2

Compounds of the formula (200)

| No. | D | X | G | Melting point °C. | $D_{max}$ |
|-----|---|---|---|---|---|
| 201 | H | S | $-n-C_5H_{11}$ | 70–72 | 0.75 |
| 202 | H | S | $-n-C_6H_{13}$ | 141–145 | 0.55 |
| 203 | H | S | $-n-C_7H_{15}$ | 140–142 | 0.29 |
| 204 | H | S | $-n-C_8H_{17}$ | 138–141 | 0.24 |
| 205 | H | S | $-n-C_9H_{19}$ | 134–136 | 0.31 |
| 206 | H | S | $-n-C_{10}H_{21}$ | 145–147 | 0.56 |
| 207 | H | S | $-n-C_{12}H_{25}$ | oil | 0.44 |
| 208 | H | S | $-CH(C_3H_7)(C_4H_9)$ | 136–138 | 0.28 |
| 209 | H | S | $-n-C_{18}H_{37}$ | 45–48 | 0.84 |
| 210 | H | S | $-CH_2-C_6H_5$ | 64–67 | 0.55 |
| 211 | $CH_3$ | S | $-CH_2-C_6H_5$ | 62–65 | 0.98 |
| 212 | $C_6H_5-CH_2-$ | S | $-CH_3$ | 54–57 | 0.69 |
| 213 | $-n-C_3H_7$ | S | $-n-C_4H_9$ | 89–92 | 0.80 |

TABLE 2-continued

Compounds of the formula $$\text{(200)}$$

(structure shown with substituents D, X–G, Cl, and NH–CO(CH$_2$)$_3$–O– linked to di-tert-alkyl phenyl group)

| No. | D | X | G | Melting point °C. | D$_{max}$ |
|---|---|---|---|---|---|
| 214 | —CH$_3$ | Se | —n-C$_8$H$_{17}$ | 40–43 | 0.21 |
| 215 | H | S | —n-C$_4$H$_9$ | 169–172 | 1.27 |
| 216 | CH$_3$— | Se | —n-C$_6$H$_{13}$ | 98–100 | 0.13 |
| 217 | CH$_3$— | Se | —n-C$_7$H$_{15}$ | 116–117 | 0.24 |
| 218 | CH$_3$— | Se | —n-C$_4$H$_9$ | 63–65 | 1.01 |
| 219 | CH$_3$— | Se | —n-C$_{10}$H$_{21}$ | 75–77 | 0.21 |
| 220 | CH$_3$— | Se | —n-C$_{12}$H$_{25}$ | 40–43 | 0.37 |

USE EXAMPLES

Example 1

Coupler Emulsion 0.05 mmol of the coupler of the formula (203) is dissolved in 2.0 ml of tricresyl phosphate/methylene chloride (1:9). The methylene chloride is evaporated off, 6.6 ml of 6% gelatin solution, 1.2 ml of water and 2.0 ml of an 8% aqueous solution of sodium isopropylnaphthalenesulphonate are added, the pH value of the mixture is adjusted to 6.5 and the mixture is emulsified for 5 minutes with the aid of an ultrasonic apparatus which has a power of 100 watts.

Coating 2.5 ml of the so obtained coupler emulsion, 1.6 ml of a silver bromide emulsion which has a pH of 6.5 and contains 1.4% of silver and 6.0% of gelatin, 1.0 ml of a 1% aqueous solution of the hardener of the formula

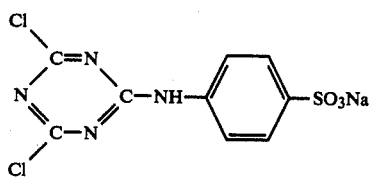

and 5.0 ml of water are mixed together and coated at 40° C. onto a substrated 13 cm × 18 cm glass plate. After the coating has solidified at 10° C., the plate is dried in a drying cabinet with circulating air, at room temperature.

Photographic exposure and processing

A strip, cut to 4.0 cm × 6.5 cm, is exposed under a step wedge for 2 seconds with 500 Lux/cm$^2$ and then treated at 24° C. as follows:

|   | Minutes |
|---|---|
| 1. Colour developing | 5 |
| 2. Washing | 5 |
| 3. First fixing | 2 |
| 4. Washing | 2 |
| 5. Silver bleaching | 2 |
| 6. Washing | 2 |
| 7. Second fixing | 4 |
| 8. Washing | 10 |
| 9. Drying | 10 |

The processing solutions have the following composition:

| I. Colour developer solution (pH = 10.7) | |
|---|---|
| 4-amino-3-methyl-N—ethyl-N—β-(methyl-sulphonamido)ethylaniline; 1½ H$_2$SO$_4$.H$_2$O | 10 mmols |
| anhydrous sodium sulphite | 2.0 g |
| potassium bromide | 0.5 g |
| potassium carbonate | 40.0 g |
| benzyl alcohol | 10.0 g |
| water | to make up to 1,000 g |
| II. Fixing solution (pH = 4.5) | |
| sodium thiosulphate.6 H$_2$O | 80.0 g |
| anhydrous sodium sulphite | 5.0 g |
| sodium borate (borax) | 6.0 g |
| potassium alum | 7.0 g |
| acetic acid | 4.0 g |
| water | to make up to 1,000 g |
| III. Silver bleaching bath (pH = 7.2) | |
| potassium ferricyanide | 100.0 g |
| boric acid | 10.0 g |
| sodium borate (borax) | 5.0 g |
| water | to make up to 1,000 g |

A yellow coloured wedge with an absorption maximum at 443 nm and a maximum colour density of 0.29 is obtained.

Photographic materials can also be produced in the same way using the other yellow couplers described in Table 2 and these materials can be processed correspondingly. The colour densities obtained have already been listed in Table 2. If the colour coupler of the formula

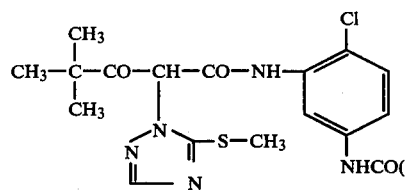 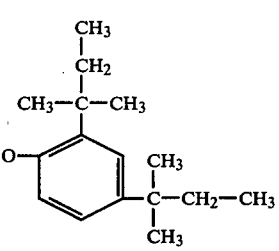

(German Offenlegungsschrift No. 2,528,638, and compound No. 15 of this specification) is employed in place of the compounds according to the invention, a yellow wedge with a maximum colour density of 1.69 is obtained.

EXAMPLE 2

Use of the DIR couplers to reduce contrast and density of colour couplers.

Coating

A blue-sensitised silver iodide/bromide emulsion (8.8% of iodide), which contains 40 mg of gelatin and 20 mg of silver, 6.4 mg of the magenta coupler 3-{3-[(2,4-bis-[1,1-dimethylpropyl]-acetamido]-benzamido}-1-(2,4,6-trichlorophenyl)-2-pyrazolidin-5-one and 0.0048 millimol of a DIR coupler, is coated onto a triacetate base in the customary manner. For comparison, a base is coated with an emulsion which is identical except that it contains no DIR coupler. The quantity data for the individual components in the emulsions are based on a base area of 1 dm$^2$.

After the layer has solidified at 10° C., it is dried in a drying cabinet with circulating air, at room temperature.

Coupler emulsion

The coupler emulsions are prepared as follows:

| colour coupler | 10 g |
|---|---|
| DIR coupler | 0 to 5 mol % (based on the colour coupler) |
| tri-o-cresyl phosphate | 10 g |
| ethyl acetate | 10 g |
| gelatin (10% aqueous solution) | 80 g |
| alkylphenylethylene glycol ether-sulphonate (10% aqueous solution, wetting agent) | 20 g |
| water to make up to | 150 g |

The colour and DIR couplers are dissolved in the solvents and added to the aqueous gelatin/wetting agent solution. The mixture is emulsified with the aid of an ultrasonic apparatus or in a colloid mill.

DIR couplers Nos. 201 to 207 from Table 2 are employed.

After exposing the material behind a continuous wedge, it is treated as follows at 37.8° C.:

| 1. Colour developing | 3¼ minutes |
|---|---|
| developer bath: | |
| potassium carbonate | 37.5 g |
| sodium metabisulphite (anhydrous) | 4.25 g |
| potassium iodide | 2.0 mg |
| sodium bromide | 1.3 g |
| hydroxylamine sulphate | 2.0 g |
| 4-(N—ethyl-N—β-hydroxyethylamino)- | |

| -continued | |
|---|---|
| 2-methylaniline sulphate | 4.75 g |
| water to make up to | 1 l |
| 2. Bleaching | 6½ minutes |
| bleaching bath: | |
| ammonium bromide | 150 g |
| ammonium salt of the iron-III complex of ethylenediamine-tetraacetic acid | 175 ml |
| acetic acid (glacial acetic acid) | 10.5 ml |
| sodium nitrate | 35 g |
| water to make up to | 1 l |
| 3. Washing | 3¼ minutes |
| 4. Fixing | 6½ minutes |
| fixing bath: | |
| ammonium thiosulphate (50%, aqueous) | 16.2 ml |
| diethylenetriaminepentaacetic acid | 1.25 g |
| sodium metabisulphite (anhydrous) | 12.4 g |
| sodium hydroxide | 2.4 g |
| water to make up to | 1 l |
| 5. Washing | 3¼ minutes |
| 6. Stabilising | 1½ minutes |
| stabiliser bath: | |
| formaldehyde (35% aqueous solution) | 5.0 ml |
| water to make up to | 1 l |

The magenta image formed is measured densitometrically. Table 3 shows the influence of the DIR couplers on the contrast and the maximum density, compared with photographic layers (without DIR couplers) which have been exposed and processed analogously.

TABLE 3

| DIR Coupler No. | Contrast ($\gamma_{max}$) | Decrease in the density (%) ($D_{max}$) |
|---|---|---|
| 201 | 32.5 | 13 |
| 202 | 50.3 | 28.6 |
| 203 | 55.6 | 40 |
| 204 | 58.3 | 51.6 |
| 205 | 59 | 51.6 |
| 206 | 39 | 34.6 |
| 207 | 42.4 | 36.4 |
| 215 (Comparison) | 14 | 7.4 |

EXAMPLE 3

Cellulose acetate bases are coated with blue-sensitised silver iodide/bromide emulsions in accordance with Example 2, the following amounts of magenta coupler and DIR coupler being used:

| Magenta coupler (mg/dm$^2$) | DIR coupler (0.0048 mmol) |
|---|---|
| 10.5 | 201 |
| 15.3 | 202 |
| 17.7 | 203 |
| 19.1 | 204 |
| 19.5 | 205 |

-continued

| Magenta coupler (mg/dm²) | DIR coupler (0.0048 mmol) |
|---|---|
| 11.9 | 206 |
| 12.8 | 207 |
| 6.4 | without DIR coupler (comparison) |

In order to determine the resolution of the layers, these are exposed through a line and space chart (mire) at various exposures.

After passing through the various treatment stages as described in Example 2, the resolution is measured through a green filter using a microdensitometer. An average value over a suitable exposure range is given in Table 4 below.

The resolution in % which is given in Table 4 below, and also in Table 5 which relates to Example 4, is determined by a modified method for determination of the modulation/transfer function, a line screen with a right-angle profile being used in place of the sine wave screen. The area covered by the line screen is 50%. The percentages quoted, which are a measure of the resolution, are based on the average difference in the densities between the images of the screen lines and those of the interspaces. The average difference in density at the lowest spatial frequency included (0.4 line/mm) is taken as 100%.

TABLE 4

| DIR Coupler No. | Contrast ($\gamma_{max}$) | Density ($D_{max}$) | Resolution % 10 lines/mm | Resolution % 30 lines/mm |
|---|---|---|---|---|
| 201 | 1.46 | 2.68 | 82 | 54 |
| 202 | 1.38 | 2.58 | 85 | 55 |
| 203 | 1.40 | 2.46 | 81 | 52 |
| 204 | 1.44 | 2.49 | 76 | 49 |
| 205 | 1.48 | 2.49 | 76 | 48 |
| 206 | 1.42 | 2.37 | 81 | 50 |
| 207 | 1.52 | 2.49 | 79 | 49 |
| without DIR coupler (comparison) | 1.65 | 2.32 | 72 | 45 |

A distinct improvement in the sharpness of the image can be achieved by the use of the DIR couplers.

EXAMPLE 4

A blue-sensitised silver halide emulsion, which contains 50 mg of gelatin, 50 mg of silver, 7.9 mg of the yellow coupler 5-{γ-[2,4-bis-(1,1-dimethylpropyl)-phenoxy]-butyramido}-2-chloro-α-[5-isopropyl-2-(4-tolylsulphonylimino)-Δ⁴-1,3,4-thiadiazolin-3-yl]-α-pivalylacetanilide, 7.9 mg of the magenta coupler according to Example 2, 6.6 mg of the cyan coupler 2-{4-[2,4-bis-(1,1-dimethylpropyl)-phenoxy]-butylcarbamoyl}-1-naphthol and 0.75 mg of the DIR coupler of the formula (202), is coated onto a cellulose acetate base in a conventional manner and, after it has solidified, is dried. The quantity data are based on 1 dm² of base area.

For comparison, a cellulose acetate base is coated with a silver halide/gelatin emulsion which contains 5.3 mg of the yellow coupler, 5.3 mg of the magenta coupler and 4.4 mg of the cyan coupler but does not contain any DIR coupler.

The sensitivity and the contrast of the two silver halide layers are approximately equal.

In order to determine the sharpness of the image, the two layers are exposed through a line and space chart (mire) at various exposures and then treated as described in Example 2. The resolution is determined behind a blue filter using a microdensitometer. The results are given in Table 5.

TABLE 5

| DIR Coupler No. | Contrast ($\gamma_{max}$) | Printing range ($\Delta$ log E) | Resolution % 10 lines/mm | Resolution % 20 lines/mm |
|---|---|---|---|---|
| 202 | 0.58 | 2.10 | 106[1] | 90 |
| without DIR coupler (comparison) | 0.64 | 1.29 | 86 | 68 |

[1]Due to the measuring method, the contrast measured here is somewhat greater than for the lowest spatial frequency of 0.4 lines/mm.

The results show the influence of the DIR couplers on that section of the coloured image which absorbs blue light. The magenta and cyan couplers were used only in order to increase the visual density, so that sharp adjustment on the developed image is facilitated.

The results show that the resolution and the printing range can be distinctly improved when DIR couplers are used in the silver halide emulsions.

The printing range is defined as the quotient of the difference in densities ($D_{max} - D_{min}$) and the contrast ($\gamma$).

What is claimed is:

1. A light-sensitive colour photographic material which contains on a support in at least one silver halide emulsion layer containing a color-coupler capable of forming a high density image dye or in an inter-layer being free of silver halide and adjacent to said emulsion layer at least one DIR-coupler in an amount of 0.1 to 100% by weight, based on the weight of the color coupler, at least one DIR-coupler, wherein the DIR coupler has the formula

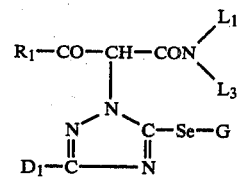

in which $D_1$ is hydrogen, alkyl having 1 to 4 carbon atoms, benzyl or chlorine and $L_3$ is phenyl or phenyl substituted by alkoxy having 1 to 5 carbon atoms, chlorine, acylamino or carboxamido, the two last mentioned radicals optionally carry ballast groups on the nitrogen atoms, $R_1$ is straight-chain or branched alkyl having 3 to 10 carbon atoms, phenyl or phenyl substituted by halogen, alkyl or alkoxy, each having 1 to 4 carbon atoms, or the radicals —OCH$_2$O— and —OCH$_2$CH$_2$O—, $L_1$ is hydrogen or alkyl having 1 to 5 carbon atoms and G is a substituted or unsubstituted aliphatic hydrocarbon radical having 1 to 18 carbon atoms, the sum of the carbon atoms in the substituents $D_1$ and G being at least 5.

2. A colour photographic material according to claim 1, wherein the DIR coupler has the formula

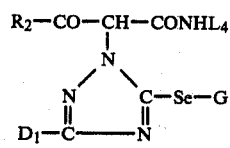

in which $R_2$ is phenyl, tert.-butyl or a radical of the formulae

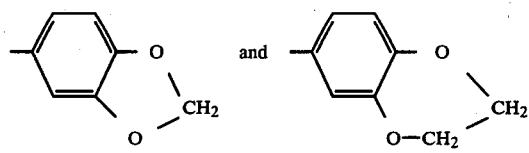

and $L_4$ is a radical of the formula

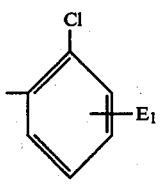

in which $R_1$ is a radical of the formulae

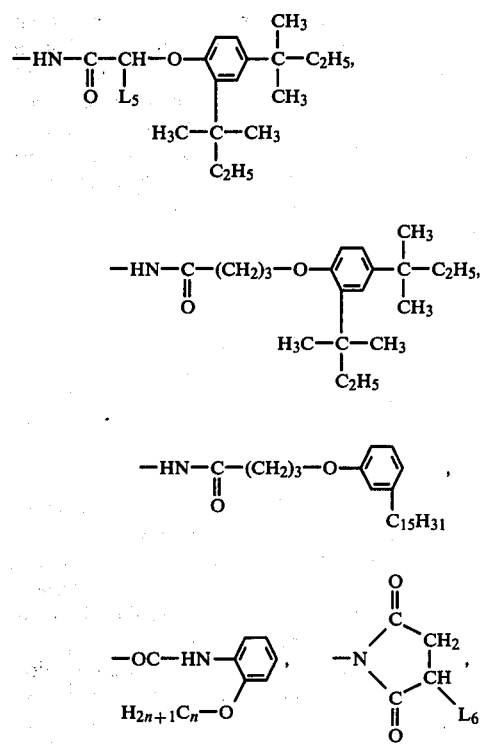

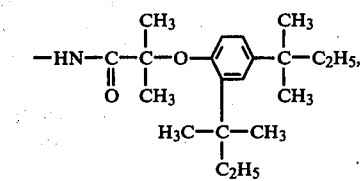

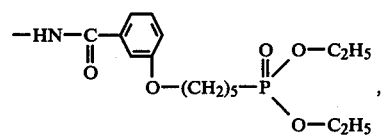

-continued

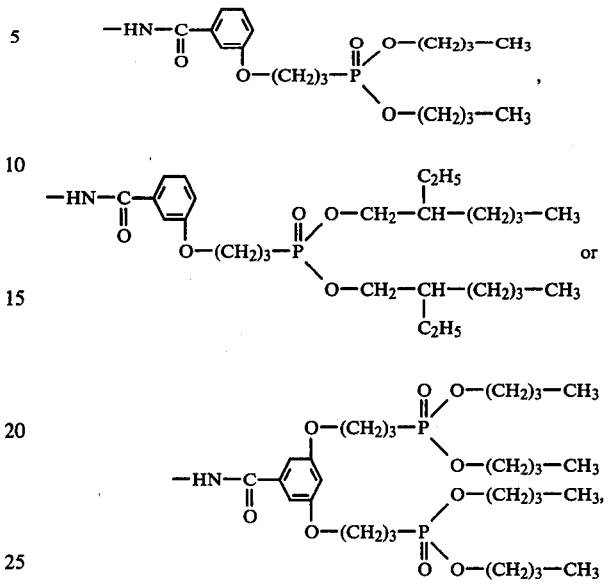

in which $L_5$ is hydrogen, ethyl or n-dodecyl, $L_6$ is n-dodecyl or n-octadecyl and n is a number from 8 to 18, $D_1$ is hydrogen, alkyl having 1 to 4 carbon atoms, benzyl or chloride and G is a substituted or unsubstituted aliphatic hydrocarbon radical of 1 to 18 carbon atoms.

3. A colour photographic material according to claim 2, wherein the DIR coupler has the formula

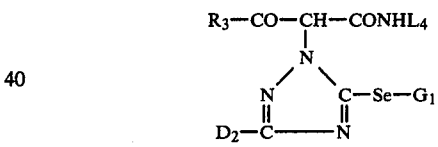

in which $R_3$ is phenyl or tert.-butyl, $G_1$ is alkyl having 1 to 18 carbon atoms or benzyl and $D_2$ is hydrogen, methyl, ethyl, propyl or butyl, the sum of the carbon atoms in the substituents $D_2$ and $G_1$ being at least 5, and $L_4$ is as defined in claim 2.

4. A colour photographic material according to claim 3, wherein the DIR coupler has the formula

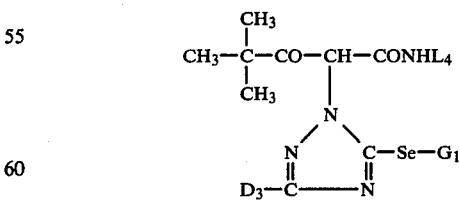

in which $D_3$ is hydrogen or methyl, the sum of the carbon atoms in the substituents $D_3$ and $G_1$ is at least 5 and $G_1$ and $L_4$ are as defined in claim 3.

5. A colour photographic material according to claim 3, wherein the DIR coupler has the formula

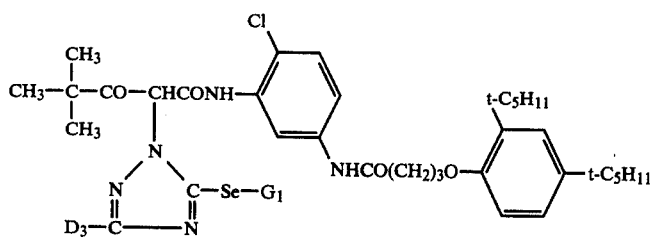

in which $D_3$ and $G_1$ are as defined in claim 4.

6. A colour photographic material according to claim 3, wherein the DIR coupler has the formula

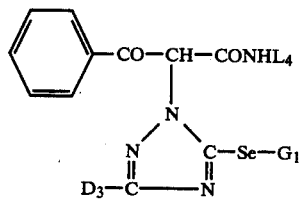

in which $D_3$ is hydrogen or methyl, the sum of the carbon atoms in the substituents $D_3$ and $G_1$ is at least 5 and $C_1$ and $L_4$ are as defined in claim 3.

7. In a method of reducing contrast and dye density generated by a color forming coupler in a color photographic material containing on a support at least one silver halide emulsion layer with said color coupler capable of forming a high density image, and an interlayer being free of silver halide and adjacent to said emulsion layer, the improvement which comprises incorporating into the layer containing the color forming coupler or into the interlayer at least one DIR-coupler in an amount of 0.1 to 100% by weight, based on the weight of the color coupler, the DIR-coupler being of the formula

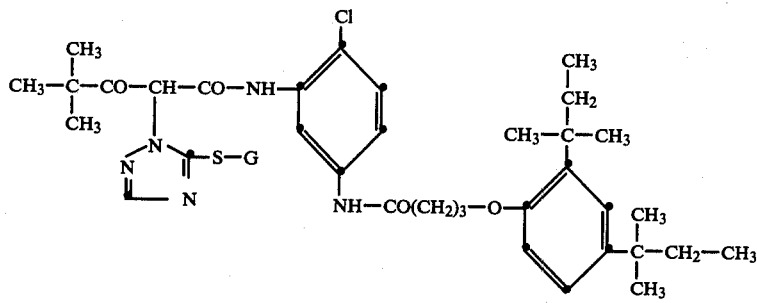

* * * * *